(12) United States Patent
Odom et al.

(10) Patent No.: US 7,491,202 B2
(45) Date of Patent: *Feb. 17, 2009

(54) ELECTROSURGICAL FORCEPS WITH SLOW CLOSURE SEALING PLATES AND METHOD OF SEALING TISSUE

(75) Inventors: Darren Odom, Longmont, CO (US); Curt D. Hammill, Erie, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 655 days.

This patent is subject to a terminal disclaimer.

(21) Appl. No.: 11/095,123

(22) Filed: Mar. 31, 2005

(65) Prior Publication Data

US 2006/0224158 A1   Oct. 5, 2006

(51) Int. Cl.
*A61B 18/18* (2006.01)

(52) U.S. Cl. .......................... 606/51; 606/52

(58) Field of Classification Search ............. 606/51–52
See application file for complete search history.

(56) References Cited

U.S. PATENT DOCUMENTS

| | | | |
|---|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 2,002,594 A | 5/1935 | Wappler et al. |
| 2,011,169 A | 8/1935 | F.C. Wappler |
| 2,031,682 A | 2/1936 | Wappler et al. |
| 2,176,479 A | 10/1939 | Willis |
| 2,279,753 A | 4/1942 | Knopp |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,720,896 A | 3/1973 | Beierlein |

(Continued)

FOREIGN PATENT DOCUMENTS

CA    2104423    2/1994

(Continued)

OTHER PUBLICATIONS

Int'l Search Report EP 04 752343.6, dated Jul. 20, 2007.

(Continued)

*Primary Examiner*—Michael Peffley

(57) ABSTRACT

An Electrosurgical bipolar forceps for sealing tissue is disclosed which includes at least one shaft member having a jaw member disposed at a distal end thereof. The jaw members are movable from a first position in spaced relation relative to one another to at least one subsequent position wherein the jaw members cooperate to grasp tissue therebetween. Each of the jaw members including a sealing plate which communicates electrosurgical energy through tissue held therebetween. At least one of the sealing plates includes one or more adjustable stop members coupled to one or more controllers. The adjustable stop member(s) are adapted for separating the sealing plates by a predetermined gap distance and the controller(s) adapted for adjusting the adjustable stop member(s) to close the sealing plates at a predetermined rate.

10 Claims, 9 Drawing Sheets

U.S. PATENT DOCUMENTS

| | | |
|---|---|---|
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Degwitz et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,671 A | 9/1996 | Yates |

| | | | | | |
|---|---|---|---|---|---|
| 5,558,672 A | 9/1996 | Edwards et al. | 5,827,271 A | 10/1998 | Buysse et al. |
| 5,562,699 A | 10/1996 | Heimberger et al. | 5,827,279 A | 10/1998 | Hughett et al. |
| 5,569,241 A | 10/1996 | Edwardds | 5,827,281 A | 10/1998 | Levin |
| 5,569,243 A | 10/1996 | Kortenbach et al. | 5,827,323 A | 10/1998 | Klieman et al. |
| 5,571,100 A | 11/1996 | Goble et al. | 5,827,548 A | 10/1998 | Lavallee et al. |
| 5,573,424 A | 11/1996 | Poppe | 5,833,690 A | 11/1998 | Yates et al. |
| 5,573,534 A | 11/1996 | Stone | 5,843,080 A | 12/1998 | Fleenor et al. |
| 5,573,535 A | 11/1996 | Viklund | 5,849,022 A | 12/1998 | Sakashita et al. |
| 5,575,805 A | 11/1996 | Li | 5,853,412 A | 12/1998 | Mayenberger |
| 5,578,052 A | 11/1996 | Koros et al. | 5,860,976 A | 1/1999 | Billings et al. |
| 5,582,611 A | 12/1996 | Tsukagoshi et al. | 5,876,401 A | 3/1999 | Schulze et al. |
| 5,585,896 A | 12/1996 | Yamazaki et al. | 5,882,567 A | 3/1999 | Cavallaro et al. |
| 5,590,570 A | 1/1997 | LeMaire, III et al. | 5,891,141 A | 4/1999 | Rydell |
| 5,601,601 A | 2/1997 | Tal et al. | 5,891,142 A | 4/1999 | Eggers et al. |
| 5,603,711 A | 2/1997 | Parins et al. | 5,893,863 A | 4/1999 | Yoon |
| 5,603,723 A | 2/1997 | Aranyi et al. | 5,893,875 A | 4/1999 | O'Connor et al. |
| 5,611,798 A | 3/1997 | Eggers | 5,893,877 A | 4/1999 | Gampp, Jr. et al. |
| 5,620,453 A | 4/1997 | Nallakrishnan | 5,902,301 A | 5/1999 | Olig |
| 5,624,452 A | 4/1997 | Yates | 5,906,630 A | 5/1999 | Anderhub et al. |
| 5,626,578 A | 5/1997 | Tihon | 5,908,420 A | 6/1999 | Parins et al. |
| 5,626,609 A | 5/1997 | Zvenyatsky et al. | 5,908,432 A | 6/1999 | Pan |
| 5,630,833 A | 5/1997 | Katsaros et al. | 5,911,719 A | 6/1999 | Eggers |
| 5,637,110 A | 6/1997 | Pennybacker et al. | 5,913,874 A | 6/1999 | Berns et al. |
| 5,638,003 A | 6/1997 | Hall | 5,921,984 A | 7/1999 | Sutcu et al. |
| 5,643,294 A | 7/1997 | Tovey et al. | 5,925,043 A | 7/1999 | Kumar et al. |
| 5,647,869 A | 7/1997 | Goble et al. | 5,935,126 A | 8/1999 | Riza |
| 5,647,871 A | 7/1997 | Levine et al. | 5,944,718 A | 8/1999 | Dafforn et al. |
| 5,649,959 A | 7/1997 | Hannam et al. | 5,951,549 A | 9/1999 | Richardson et al. |
| 5,658,281 A | 8/1997 | Heard | 5,954,720 A | 9/1999 | Wilson et al. |
| 5,662,667 A | 9/1997 | Knodel | 5,957,923 A | 9/1999 | Hahnen et al. |
| 5,665,100 A | 9/1997 | Yoon | 5,960,544 A | 10/1999 | Beyers |
| 5,667,526 A | 9/1997 | Levin | 5,961,514 A | 10/1999 | Long et al. |
| 5,674,220 A | 10/1997 | Fox et al. | 5,964,758 A | 10/1999 | Dresden |
| 5,681,282 A | 10/1997 | Eggers et al. | 5,976,132 A | 11/1999 | Morris |
| 5,688,270 A | 11/1997 | Yates et al. | 5,984,939 A | 11/1999 | Yoon |
| 5,693,051 A | 12/1997 | Schulze et al. | 5,989,277 A | 11/1999 | LeMaire, III et al. |
| 5,695,522 A | 12/1997 | LeMaire, III et al. | 5,997,565 A | 12/1999 | Inoue |
| 5,700,261 A | 12/1997 | Brinkerhoff | 6,004,335 A | 12/1999 | Vaitekunas et al. |
| 5,702,390 A | 12/1997 | Austin et al. | 6,010,516 A | 1/2000 | Hulka et al. |
| 5,707,369 A | 1/1998 | Vaitekunas et al. | 6,024,741 A | 2/2000 | Williamson et al. |
| 5,709,680 A | 1/1998 | Yates et al. | 6,024,744 A | 2/2000 | Kese et al. |
| 5,716,366 A | 2/1998 | Yates | 6,030,384 A | 2/2000 | Nezhat |
| 5,720,744 A | 2/1998 | Eggleston et al. | 6,033,399 A | 3/2000 | Gines |
| 5,722,421 A | 3/1998 | Francese et al. | 6,039,733 A | 3/2000 | Buysse et al. |
| 5,725,536 A | 3/1998 | Oberlin et al. | 6,041,679 A | 3/2000 | Slater et al. |
| 5,727,428 A | 3/1998 | LeMaire, III et al. | 6,050,996 A | 4/2000 | Schmaltz et al. |
| 5,735,848 A | 4/1998 | Yates et al. | 6,053,914 A | 4/2000 | Eggers et al. |
| 5,743,906 A | 4/1998 | Parins et al. | 6,053,933 A | 4/2000 | Balazs et al. |
| 5,755,717 A | 5/1998 | Yates et al. | D424,694 S | 5/2000 | Tetzlaff et al. |
| 5,766,130 A | 6/1998 | Selmonosky | D425,201 S | 5/2000 | Tetzlaff et al. |
| 5,766,166 A | 6/1998 | Hooven | 6,059,782 A | 5/2000 | Novak et al. |
| 5,766,170 A | 6/1998 | Eggers | 6,074,386 A | 6/2000 | Goble et al. |
| 5,769,849 A | 6/1998 | Eggers | RE36,795 E | 7/2000 | Rydell |
| 5,772,655 A | 6/1998 | Bauer et al. | 6,083,223 A | 7/2000 | Baker |
| 5,772,670 A | 6/1998 | Brosa | 6,086,586 A | 7/2000 | Hooven |
| 5,776,128 A | 7/1998 | Eggers | 6,090,107 A | 7/2000 | Borgmeier et al. |
| 5,776,130 A | 7/1998 | Buysse et al. | 6,096,037 A | 8/2000 | Mulier et al. |
| 5,779,701 A | 7/1998 | McBrayer et al. | 6,099,550 A | 8/2000 | Yoon |
| H1745 H | 8/1998 | Paraschac | 6,102,909 A | 8/2000 | Chen et al. |
| 5,792,137 A | 8/1998 | Carr et al. | 6,110,171 A | 8/2000 | Rydell |
| 5,792,177 A | 8/1998 | Kaseda | 6,113,596 A | 9/2000 | Hooven et al. |
| 5,797,927 A | 8/1998 | Yoon | 6,113,598 A | 9/2000 | Baker |
| 5,797,938 A | 8/1998 | Paraschac et al. | 6,117,158 A | 9/2000 | Measamer et al. |
| 5,797,941 A | 8/1998 | Schulze et al. | 6,123,701 A | 9/2000 | Nezhat |
| 5,797,958 A | 8/1998 | Yoon | H1904 H | 10/2000 | Yates et al. |
| 5,800,449 A | 9/1998 | Wales | 6,126,658 A | 10/2000 | Baker |
| 5,807,393 A | 9/1998 | Williamsom, IV et al. | 6,152,923 A | 11/2000 | Ryan |
| 5,810,808 A | 9/1998 | Eggers | 6,162,220 A | 12/2000 | Nezhat |
| 5,810,811 A | 9/1998 | Yates et al. | 6,174,309 B1 | 1/2001 | Wrublewski et al. |
| 5,810,877 A | 9/1998 | Roth et al. | 6,179,834 B1 | 1/2001 | Buysse et al. |
| 5,814,043 A | 9/1998 | Shapeton | 6,179,837 B1 | 1/2001 | Hooven |
| 5,817,083 A | 10/1998 | Williamson, IV et al. | 6,183,467 B1 | 2/2001 | Shapeton et al. |
| 5,820,630 A | 10/1998 | Lind | 6,187,003 B1 | 2/2001 | Buysse et al. |

| | | |
|---|---|---|
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 * | 6/2004 | Lutze et al. ............... 606/51 |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 * | 8/2004 | Bommannan et al. ....... 607/101 |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |

| | | |
|---|---|---|
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0162557 A1 | 8/2004 | Tetzlaff et al. |
| 2004/0176762 A1 | 9/2004 | Lawes et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld et al. |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |
| 2007/0213707 A1 | 9/2007 | Dumbauld et al. |

| | | | | | | |
|---|---|---|---|---|---|---|
| 2007/0213708 A1 | 9/2007 | Dumbauld et al. | | JP | 501068 | 9/1984 |
| 2007/0213712 A1 | 9/2007 | Buysse et al. | | JP | 502328 | 3/1992 |
| 2007/0255279 A1 | 11/2007 | Buysse et al. | | JP | 5-5106 | 1/1993 |
| 2007/0260235 A1 | 11/2007 | Podhajsky | | JP | 5-40112 | 2/1993 |
| 2007/0260238 A1 | 11/2007 | Guerra | | JP | 5-40112 | 5/1993 |
| 2007/0260241 A1 | 11/2007 | Dalla Betta et al. | | JP | 06343644 A2 | 12/1994 |
| 2007/0260242 A1 | 11/2007 | Dycus et al. | | JP | 07265326 A2 | 10/1995 |
| 2007/0265616 A1 | 11/2007 | Couture et al. | | JP | 07265328 A2 | 10/1995 |
| 2008/0004616 A1 | 1/2008 | Patrick | | JP | 08056955 A2 | 3/1996 |
| 2008/0009860 A1 | 1/2008 | Odom | | JP | 08252263 A2 | 10/1996 |
| 2008/0015575 A1 | 1/2008 | Odom et al. | | JP | 09010223 A2 | 1/1997 |
| 2008/0021450 A1 | 1/2008 | Couture | | JP | 11244298 A2 | 9/1999 |
| 2008/0033428 A1 | 2/2008 | Artale et al. | | JP | 2000342599 A2 | 12/2000 |
| 2008/0039835 A1 | 2/2008 | Johnson et al. | | JP | 2000350732 A2 | 12/2000 |
| 2008/0045947 A1 | 2/2008 | Johnson et al. | | JP | 2001008944 A2 | 1/2001 |
| 2008/0058802 A1 | 3/2008 | Couture et al. | | JP | 2001029356 A2 | 2/2001 |
| 2008/0082100 A1 | 4/2008 | Orton et al. | | JP | 2001128990 A2 | 5/2001 |
| | | | | RU | 401367 | 11/1974 |
| FOREIGN PATENT DOCUMENTS | | | | SU | 401367 | 10/1973 |
| | | | | WO | WO02/080784 | 10/1972 |
| DE | 2415263 | 10/1975 | | WO | WO89/00757 | 1/1989 |
| DE | 2627679 | 1/1977 | | WO | WO 92/04873 | 4/1992 |
| DE | 8712328 | 3/1988 | | WO | WO 92/06642 | 4/1992 |
| DE | 4303882 | 8/1994 | | WO | WO 94/08524 A | 4/1994 |
| DE | 29616210 | 1/1997 | | WO | WO94/20025 | 9/1994 |
| DE | 19608716 | 4/1997 | | WO | WO 95/02369 | 1/1995 |
| DE | 19751106 | 5/1998 | | WO | WO95/07662 | 3/1995 |
| DE | 19751108 | 5/1999 | | WO | WO 95/07662 | 3/1995 |
| EP | 0364216 A1 | 4/1990 | | WO | WO95/15124 | 6/1995 |
| EP | 518230 A1 | 12/1992 | | WO | WO96/05776 | 2/1996 |
| EP | 0 541 930 B1 | 5/1993 | | WO | WO 96/022056 | 7/1996 |
| EP | 0572131 | 12/1993 | | WO | WO 96/13218 | 9/1996 |
| EP | 584787 A1 | 3/1994 | | WO | WO 97/00647 | 1/1997 |
| EP | 0589453 A2 | 3/1994 | | WO | WO 97/00648 | 1/1997 |
| EP | 0623316 A1 | 11/1994 | | WO | WO 97/10764 | 3/1997 |
| EP | 0624348 A2 | 11/1994 | | WO | WO97/10764 | 3/1997 |
| EP | 0650701 A1 | 5/1995 | | WO | WO 97/24073 | 7/1997 |
| EP | 0717966 A1 | 6/1996 | | WO | WO 97/24993 | 7/1997 |
| EP | 0694290 A3 | 9/1996 | | WO | WO 98/27880 | 7/1998 |
| EP | 0754437 A3 | 3/1997 | | WO | WO 99/03407 | 1/1999 |
| EP | 853922 A1 | 7/1998 | | WO | WO 99/03408 | 1/1999 |
| EP | 0875209 A1 | 11/1998 | | WO | WO 99/03409 | 1/1999 |
| EP | 0878169 A1 | 11/1998 | | WO | WO 99/12488 | 3/1999 |
| EP | 0887046 A3 | 1/1999 | | WO | WO 99/40857 | 8/1999 |
| EP | 0923907 A1 | 6/1999 | | WO | WO 99/040861 | 8/1999 |
| EP | 0986990 A1 | 3/2000 | | WO | WO 99/51158 | 10/1999 |
| EP | 1034747 A1 | 9/2000 | | WO | WO 99/066850 | 12/1999 |
| EP | 1034748 A1 | 9/2000 | | WO | WO 99/66850 A | 12/1999 |
| EP | 1025807 A3 | 10/2000 | | WO | WO 00/24330 | 5/2000 |
| EP | 1034746 A3 | 10/2000 | | WO | WO00/24331 | 5/2000 |
| EP | 1050278 A1 | 11/2000 | | WO | WO 00/24331 | 5/2000 |
| EP | 1053719 A1 | 11/2000 | | WO | WO 00/41638 | 7/2000 |
| EP | 1053720 A1 | 11/2000 | | WO | WO00/47124 | 8/2000 |
| EP | 1055399 A1 | 11/2000 | | WO | WO 00/53112 | 9/2000 |
| EP | 1055400 A1 | 11/2000 | | WO | WO 01/17448 A | 3/2001 |
| EP | 1080694 A1 | 3/2001 | | WO | WO 01/54604 | 8/2001 |
| EP | 1082944 A1 | 3/2001 | | WO | WO 02/07627 | 1/2002 |
| EP | 1159926 A2 | 12/2001 | | WO | WO02/07627 | 1/2002 |
| EP | 1301135 A | 4/2003 | | WO | WO 02/067798 A1 | 9/2002 |
| EP | 1330991 A1 | 7/2003 | | WO | WO 02/080783 | 10/2002 |
| EP | 1488177 A2 | 6/2004 | | WO | WO02/080783 | 10/2002 |
| EP | 1472984 A1 | 11/2004 | | WO | WO 02/080784 | 10/2002 |
| EP | 1527747 A2 | 5/2005 | | WO | WO02/080785 | 10/2002 |
| EP | 1530952 A1 | 5/2005 | | WO | WO 02/080785 | 10/2002 |
| EP | 1532932 A1 | 5/2005 | | WO | WO02/080786 | 10/2002 |
| EP | 1535581 A2 | 6/2005 | | WO | WO 02/080786 | 10/2002 |
| EP | 1609430 A1 | 12/2005 | | WO | WO 02/080793 | 10/2002 |
| EP | 1632192 A1 | 3/2006 | | WO | WO02/080793 | 10/2002 |
| EP | 1645238 A1 | 4/2006 | | WO | WO 02/080794 | 10/2002 |
| EP | 1645240 A2 | 4/2006 | | WO | WO02/080794 | 10/2002 |
| EP | 1707143 A1 | 10/2006 | | WO | WO 02/080795 | 10/2002 |
| GB | 2214430 A | 6/1989 | | WO | WO 02/080796 | 10/2002 |
| GB | 2213416 | 8/1989 | | WO | WO02/080797 | 10/2002 |

| | | |
|---|---|---|
| WO | WO 02/080797 | 10/2002 |
| WO | WO 02/080798 A1 | 10/2002 |
| WO | WO 02/080799 | 10/2002 |
| WO | WO02/081170 | 10/2002 |
| WO | WO 02/081170 | 10/2002 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO2004/032777 | 4/2004 |
| WO | WO 2004/052221 A1 | 6/2004 |
| WO | WO 04/082495 A1 | 9/2004 |
| WO | WO 2004/073488 A2 | 9/2004 |
| WO | WO 2004/073490 | 9/2004 |
| WO | WO2004/073490 | 9/2004 |
| WO | WO2004/073753 | 9/2004 |
| WO | WO 2004/082495 | 9/2004 |
| WO | WO 2004/098383 A1 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |

OTHER PUBLICATIONS

Int'l Search Report EP 06 024122.1, dated Mar. 19, 2007.
Int'l Search Report EP 07 001480.8, dated Apr. 12, 2007.
Int'l Search Report EP 07 001488.1, dated May 29, 2007.
Int'l Search Report—Extended EP 07 009029.5, dated Jul. 12, 2007.
Int'l Search Report EP 07 009321.6, dated Aug. 17, 2007.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l S Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 19, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan. 2004.
Johnson et al. "Evaluation of a Bipolar electrothermal Vessel Sealing Device in Hemorrhoidectomy" Sales Product Literature; Jan. 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing"Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique"Annals Of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washinton, D.C.
Levy et al. "Use of a New Energy-based Vessel Ligation Device During Vaginal Hysterectomy"Int'l Federation of Gynecology and Obstetrics (FIGO) World Congress.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing in Minimally Invasive Surgery in Children" Int'l Pediatric Endosurgery Group (IPEG) 2000.
Palazzo et al. "Randomized clinical trial of Ligasure versus open haemorrholdectomy" British Journal of Surgery 2002, 89, 154-157.
"Innovations in Electrosurgery" Sales/Product Literature.
LigaSure Vessel Sealing System, the Seal of Confidence in General, Gynecologic, Urologic, and Laparaoscopic Surgery Sales/Product Literature.
Carbonell et al., "Comparison of theGyrus PlasmaKinetic Sealer and the Valleytab LigaSure Device in the Hemostasis of Small, Medium, and Large-Sized Arterles" Carolinas Laparaoscopic and Advanced Surgery Program, Carolinas Medical Center, Charlotte, NC.
"Reducing Needlestick Injuries in the Operating Room" Sales/Product Literature.
Chung et al., "Clinical Experience of Sutureless Closed Hemorrhoidectomy with LigaSure" Diseases of the Colon & Rectum vol. 48, No. 1 Jan. 2003.
Strasberg et al., "Use of Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, ☐Apr. 2001 pp. 236-237.
W. Scott Helton, "LigaSure Vessel Sealing System: Revolutionary Hemostasis Product for General Surgery" Sales/Product Literature.
Michael Choti, "Abdominoperineal Resection with the LigaSure Vessel Sealing System and LigaSure Atlas 20 cm Open Instrument" Innovations That Work, ☐Jun. 2003.
Craig Johnson, "Use of the LigaSure Vessel Sealing System in Bloodless Hemorrhoidectomy" Innovations That Work, ☐Mar. 2000.
Muller et al., "Extended Left Hemicolectomy Using the LigaSure Vessel Sealing System" Innovations That Work, ☐Sep. 1999.
Herman et al., "Laparoscopic Intestinal Resection With the LigaSure Vessel Sealing System: A Case Report" Innovations That Work, ☐Feb. 2002.

Carus et al., "Initial Experience With the LigaSure Vessel Sealing System in Abdominal Surgery" Innovations That Work, ☐Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing For Hemostasis During Gynecologic Surgery" Sales/Product Literature.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson et al. "Radical Cystectomy in Females" Current Surgical Techniques in Urology, vol. 14, Issue 3.

E. David Crawford "Use of a Novel Vessel Sealing Technology in Management of the Dorsal Veinous Complex" Sales/Product Literature.

Jarrett et al., "Use of the LigaSure Vessel Sealing System for Perf-Hilar Vessels in Laparoscopic Nephrectomy" Sales/Product Literature.

E. David Crawford "Evaluation of a New Vessel Sealing Device in Urologic Cancer Surgery" Sales/Product Literature.

Joseph Ortenberg "LigaSure System Used in Laparoscopic 1st and 2nd Stage Orchiopexy" Innovations That Work, Nov. 2002.

Koyle., "Laparoscopic Patomo Varicocele Ligation in Children and Adolescents" Pediatric Endosurgery & Innovations Techniques, vol. 6, No. 1, 2002.

Dulemba et al. "Use of a Bipolar Electrothermal Vessel Sealer in Laparoscopically Assisted Vaginal Hysterectomy" Sales/Product Literature.

Johnson et al. "Evaluation of a Bipolar electrothermal Vessel Seating Device in Hemorrhoidectomy" Sales/Product Literaure.

Int'l Search Report PCT/US98/18640.
Int'l Search Report PCT/US98/23950.
Int'l Search Report PCT/US99/24869.
Int'l Search Report PCT/US01/11218.
Int'l Search Report PCT/US01/11340.
Int'l Search Report PCT/US01/11420.
Int'l Search Report PCT/US02/01890.
Int'l Search Report PCT/US02/11100.
Int'l Search Report PCT/US04/03436.
Int'l Search Report PCT/US04/13273.
Int'l Search Report PCT/US04/15311.
Int'l Search Report EP 98944778.
Int'l Search Report EP 98958575.
Int'l Search Report EP 04027314.
Int'l Search Report EP 04027479.
Int'l Search Report EP 04027705.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.

* cited by examiner

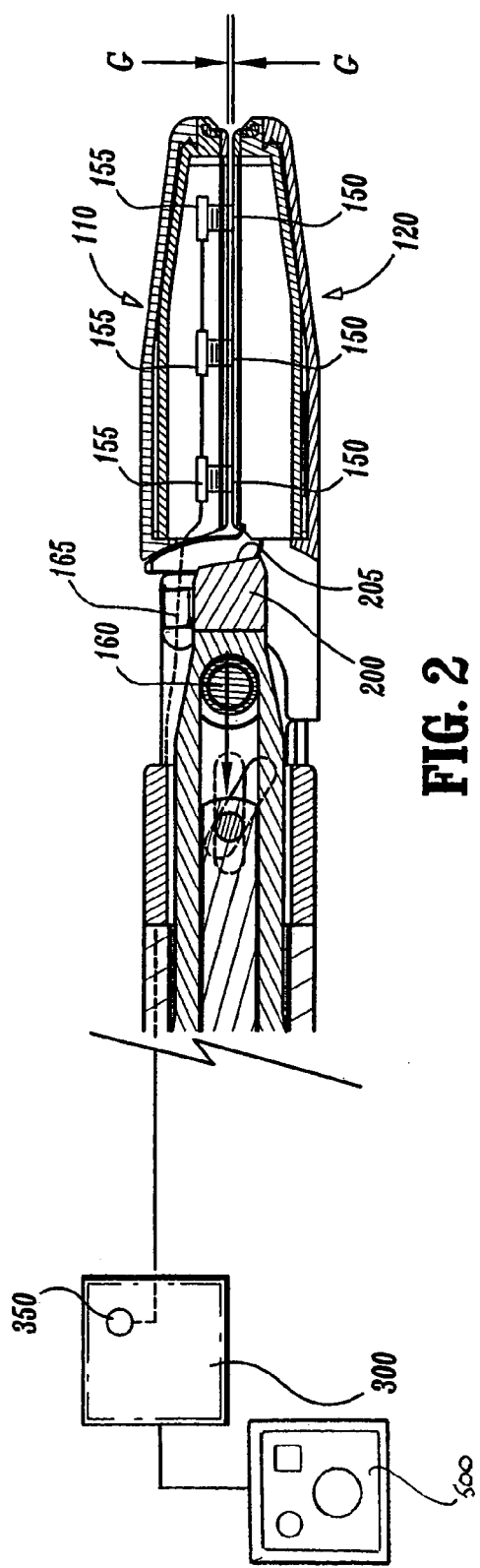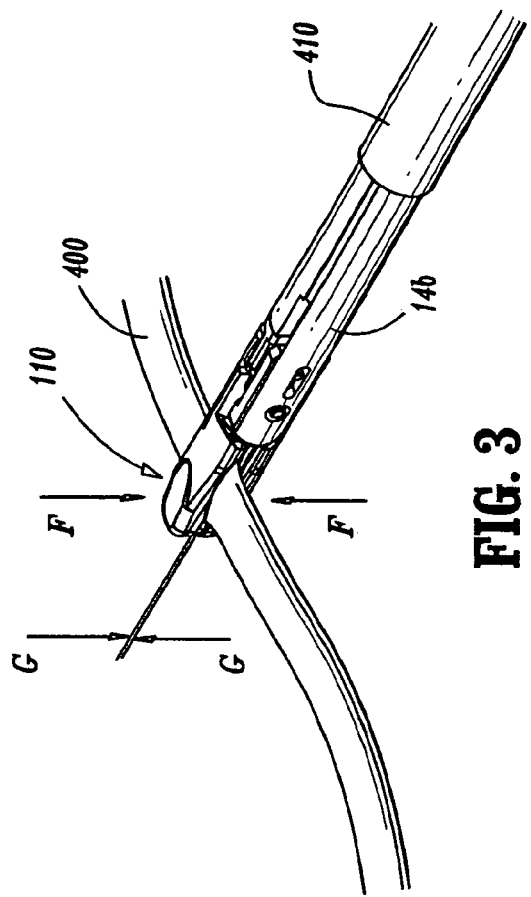
FIG. 2
FIG. 3

ELECTROSURGICAL FORCEPS WITH SLOW CLOSURE SEALING PLATES AND METHOD OF SEALING TISSUE

BACKGROUND

The present disclosure relates to an electrosurgical instrument and method for performing electrosurgical procedures. More particularly, the present disclosure relates to an open or endoscopic bipolar electrosurgical forceps including opposing jaw members which are configured to slowly close about tissue and a method of using the forceps to perform so-called "slow close" tissue sealing procedures, i.e., the sealing plates are designed to close at a specified rate and pressure to create a tissue seal of highest integrity.

TECHNICAL FIELD

A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, are used for less invasive endoscopic surgical procedures. Electrosurgical forceps (open or endoscopic) utilize mechanical clamping action and electrical energy to effect hemostasis on the clamped tissue. The forceps include electrosurgical sealing plates which apply the electrosurgical energy to the clamped tissue. By controlling the intensity, frequency and duration of the electrosurgical energy applied through the sealing plates to the tissue, the surgeon can coagulate, cauterize and/or seal tissue.

Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Since tissue sealing procedures involve more than simply cauterizing tissue, to create an effective seal the procedures involve precise control of a variety of factors. In order to affect a proper seal in vessels or tissue, it has been determined that two predominant mechanical parameters must be accurately controlled: the pressure applied to the tissue; and the gap distance between the electrodes (i.e., distance between opposing jaw members when closed about tissue).

Numerous electrosurgical instruments have been proposed in the past for various open and endoscopic surgical procedures. However, most of these instruments cauterize or coagulate tissue and are not designed to create an effective or a uniform seal.

In addition, many of the instruments of the past include blade members or shearing members which simply cut tissue in a mechanical and/or electromechanical manner and are relatively ineffective for vessel or tissue sealing purposes. Other instruments generally rely on clamping pressure alone to procure proper sealing thickness and are often not designed to take into account gap tolerances and/or parallelism and flatness requirements which are parameters which, if properly controlled, can assure a consistent and effective tissue seal. Thus, a need exists to develop an electrosurgical instrument which effectively and consistently seals tissue.

SUMMARY

The present disclosure relates to a vessel or tissue sealing instrument which is designed to manipulate, grasp and seal tissue utilizing jaw members which are configured to close about tissue at a predetermined, automatically determined or manually-induced closure rate which is contemplated to produce a highly effective tissue seal. Closure rate is particularly important and useful since it has been determined to affect the amount of collagen that is liquefied during the tissue sealing process, which has been determined to be directly related to the quality of the tissue seal. Thus, the present disclosure relates to various mechanical, electro-mechanical and electrical systems and methods which control the jaw members such that the electrically conductive sealing plates close at a predetermined rate to retain as much collagen as possible at the sealing site during sealing. More simply put, if the rate of closure is too fast, collagen may be pushed out of the sealing site, resulting in a weaker overall seal. If the closure rate is too slow, then the tissue being sealed may shrink and loose sufficient contact with the electrosurgical forceps, also possibly resulting in a weaker seal.

One embodiment according to the present disclosure relates to electrosurgical bipolar forceps for sealing tissue which includes one or more shaft members with an end effector assembly disposed at a distal end of the shaft(s). The end effector assembly includes jaw members which are movable from an open position to a closed position and, when closed, the jaw members cooperate to grasp tissue. In addition, each of the jaw members includes a sealing plate for transferring electrosurgical energy through tissue grasped by the jaw members. The sealing plates include one or more adjustable stop members which separate the sealing plates by a predetermined gap distance. The adjustable stop members are also connected to one or more controllers which adjust the adjustable stop member(s) to close the sealing plates at a predetermined rate.

The present disclosure also relates to a method for sealing tissue and includes the initial step of providing an electrosurgical bipolar forceps which includes one or more shaft members with an end effector assembly disposed at a distal end of the shaft(s). The end effector assembly includes jaw members which are movable from an open position to a closed position and, when closed, the jaw members cooperate to grasp tissue. In addition, each of the jaw members includes a sealing plate for transferring electrosurgical energy through tissue grasped by the jaw members. The sealing plates include one or more adjustable stop members which separate the sealing plates by a predetermined gap distance. The adjustable stop members are also connected to one or more controllers which adjust the adjustable stop member(s) to close the sealing plates at a predetermined rate. Other steps include extending the adjustable stop member(s) to adjust the gap distance based on one or more pre-surgical parameters and actuating the jaw members to grasp tissue between the sealing plates. The final step includes retracting the adjustable stop member(s) at the predetermined rate based upon one or more parameters to close the sealing plates around the tissue while simultaneously conducting energy to the sealing plates through the tissue to effect a tissue seal.

BRIEF DESCRIPTION OF THE DRAWINGS

Various embodiments of the present disclosure are described herein with reference to the drawings wherein:

FIG. 2 is a side, partial internal view of an end effector assembly shown in closed configuration;

FIG. 3 is a rear, perspective view of the end effector of FIG. 2 shown with tissue grasped therein;

DETAILED DESCRIPTION

Particular embodiments of the present disclosure will be described hereinbelow with reference to the accompanying drawings. In the following description, well-known functions or constructions are not described in detail to avoid obscuring the present disclosure in unnecessary detail.

Electrosurgical forceps which is configured to have sealing plates designed to close at a predetermined rate based on automatically-induced or manually-induced closure is disclosed. A method for controlling or regulating the sealing plates to close at a selected or predetermined closure rate is also discussed and described herein.

In one particular useful embodiment, the electrosurgical forceps includes at least one selectively adjustable (automatic or manual) stop member which controls the distance between the sealing plates.

Figure 1A:
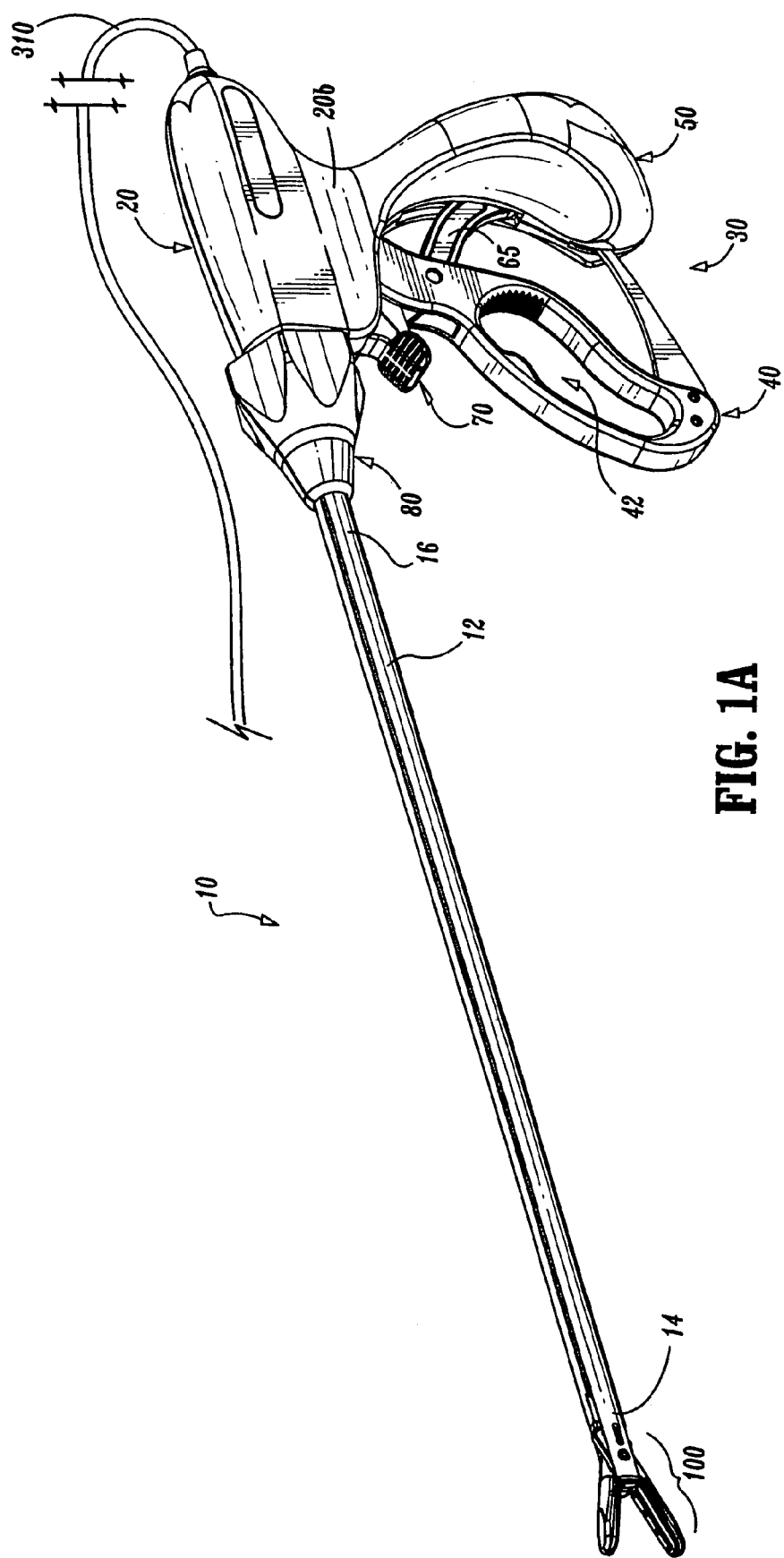
FIG. 1A is a perspective view of an endoscopic bipolar forceps which is configured to close at a predetermined rate according to the present disclosure.

More particularly and with specific reference to the figures, FIG. 1A shows an endoscopic vessel sealing bipolar forceps 10. Those skilled in the art will understand that the invention according to the present disclosure may be adapted for use with either an endoscopic instrument or an open instrument. It should also be appreciated that different electrical and mechanical connections and other considerations apply to each particular type of instrument, however, the novel aspects with respect to the sealing plates configured to close at a predetermined, automatically configured or manually-induced closure rate (hereinafter "slow closure sealing plates") and their operating characteristics remain generally consistent with respect to both the open or endoscopic designs.

The forceps 10 is shown by way of example and other electrosurgical forceps are also envisioned which allow for slow closure sealing plates of the present disclosure. In the drawings and in the description which follows, the term "proximal", refers to the end of the forceps 10 which is closer to the user, while the term "distal" refers to the end of the forceps which is further from the user.

Figure 1B:
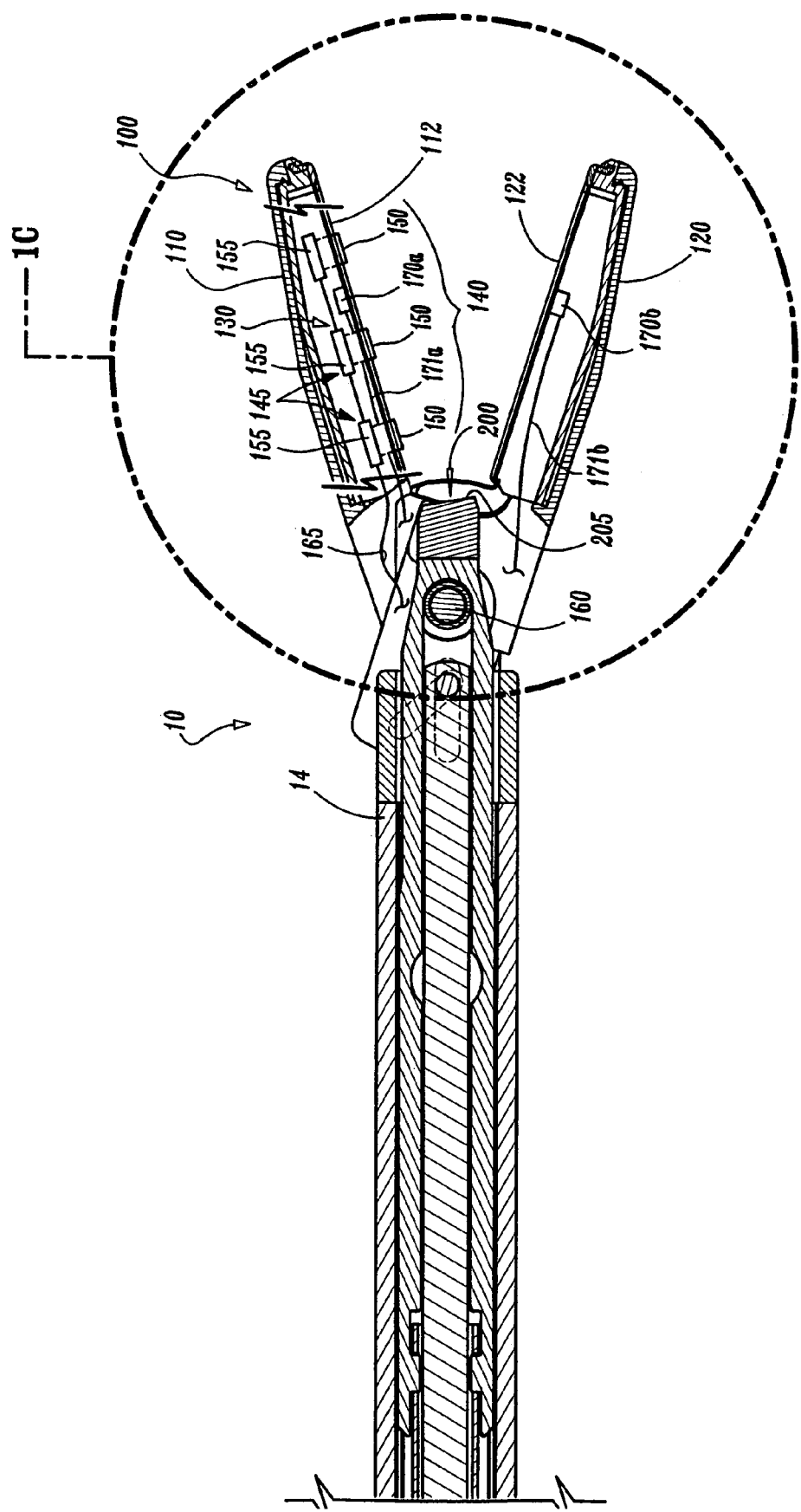
FIG. 1B is a side, partial internal view of an endoscopic forceps showing a selectively adjustable stop member assembly according to the present disclosure.
Figure 1C:
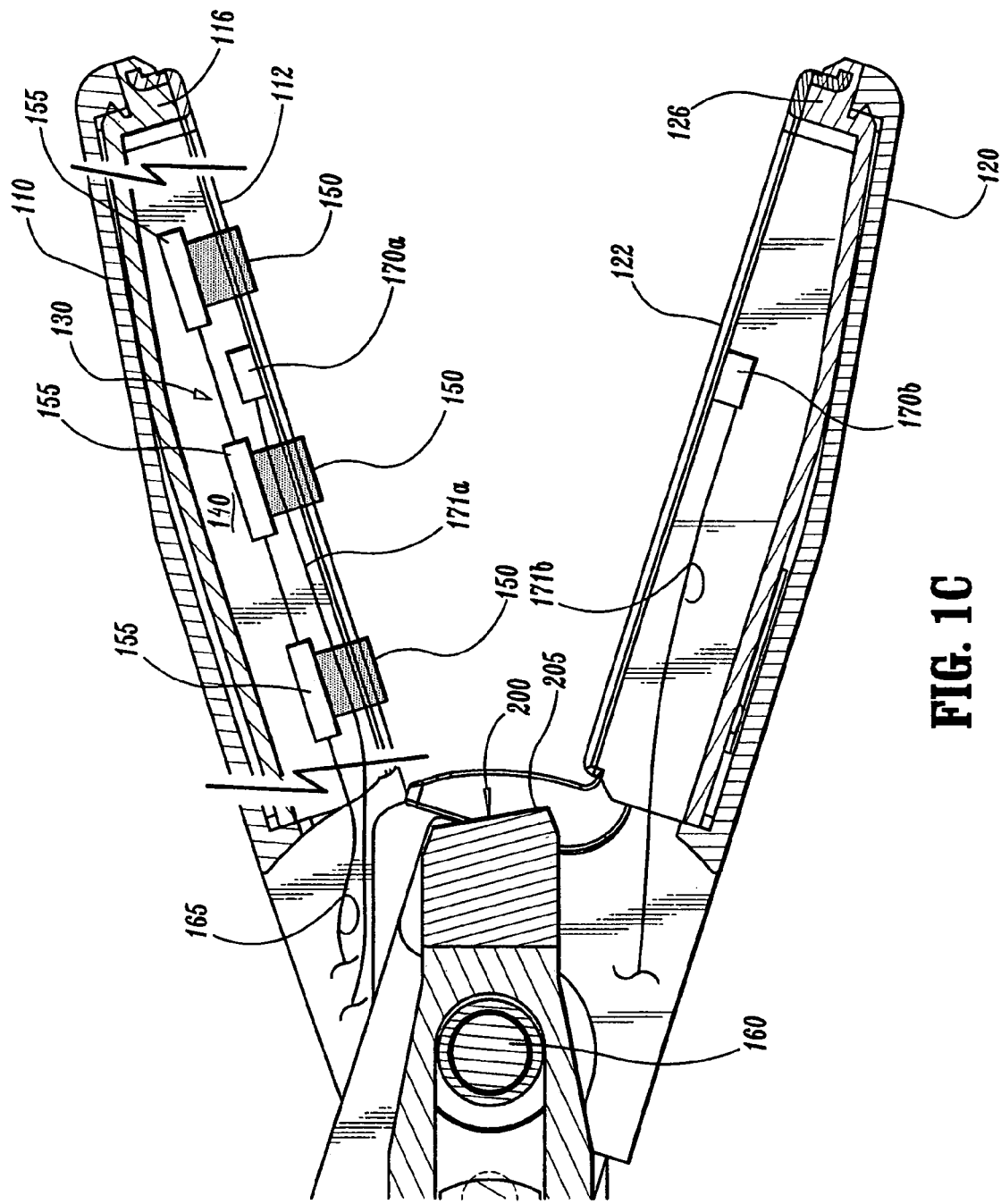
FIG. 1C is an enlarged view of the area of detail of FIG. 1B.

FIGS. 1A-1C show the forceps 10 which is configured to support an effector assembly 100. More particularly, forceps 10 generally includes a housing 20, a handle assembly 30, a rotating assembly 80, and a trigger assembly 70 which mutually cooperate with the end effector assembly 100 to grasp, seal and, if required, divide tissue. The forceps 10 also includes a shaft 12 which has a distal end 14 which mechanically engages the end effector assembly 100 and a proximal end 16 which mechanically engages the housing 20 proximate the rotating assembly 80.

The forceps 10 also includes a plug (not shown) which connects the forceps 10 to a source of electrosurgical energy, e.g., an electrosurgical generator 500, via an electrical cable 310 (See FIG. 2). Handle assembly 30 includes a fixed handle 50 and a movable handle 40. Handle 40 moves relative to the fixed handle 50 to actuate the end effector assembly 100 and enable a user to grasp and manipulate tissue 400 as shown in FIG. 3.

The end effector assembly 100 includes a pair of opposing jaw members 110 and 120 each having an electrically conductive sealing plate 112 and 122, respectively, attached thereto for conducting electrosurgical energy through tissue 400 held therebetween. More particularly, the jaw members 110 and 120 move in response to movement of the handle 40 from an open position to a closed position. In open position the sealing plates 112 and 122 are disposed in spaced relation relative to one another. In a clamping or closed position the sealing plates 112 and 122 cooperate to grasp tissue and apply electrosurgical energy thereto.

The jaw members 110 and 120 are activated using a drive assembly (not shown) enclosed within the housing 20. The drive assembly cooperates with the movable handle 40 to impart movement of the jaw members 110 and 120 from the open position to the clamping or closed position. Examples of a handle assemblies are shown and described in commonly-owned U.S. application Ser. No. 10/389,894 entitled "VESSEL SEALER AND DIVIDER AND METHOD MANUFACTURING SAME" and commonly owned U.S. application Ser. No. 10/460,926 entitled "VESSEL SEALER AND DIVIDER FOR USE WITH SMALL TROCARS AND CANNULAS" which are both hereby incorporated by reference herein in their entirety.

In addition, the handle assembly 30 of this particular disclosure includes a four-bar mechanical linkage which provides a unique mechanical advantage when sealing tissue between the jaw members 110 and 120. For example, once the desired position for the sealing site is determined and the jaw members 110 and 120 are properly positioned, handle 40 may be compressed fully to lock the electrically conductive sealing plates 112 and 122 in a closed position against the tissue. The details relating to the inter-cooperative relationships of the inner-working components of forceps 10 are disclosed in the above-cited commonly-owned U.S. patent application Ser. No. 10/369,894. Another example of an endoscopic handle assembly which discloses an off-axis, lever-like handle assembly, is disclosed in the above-cited U.S. patent application Ser. No. 10/460,926.

Figure 4:
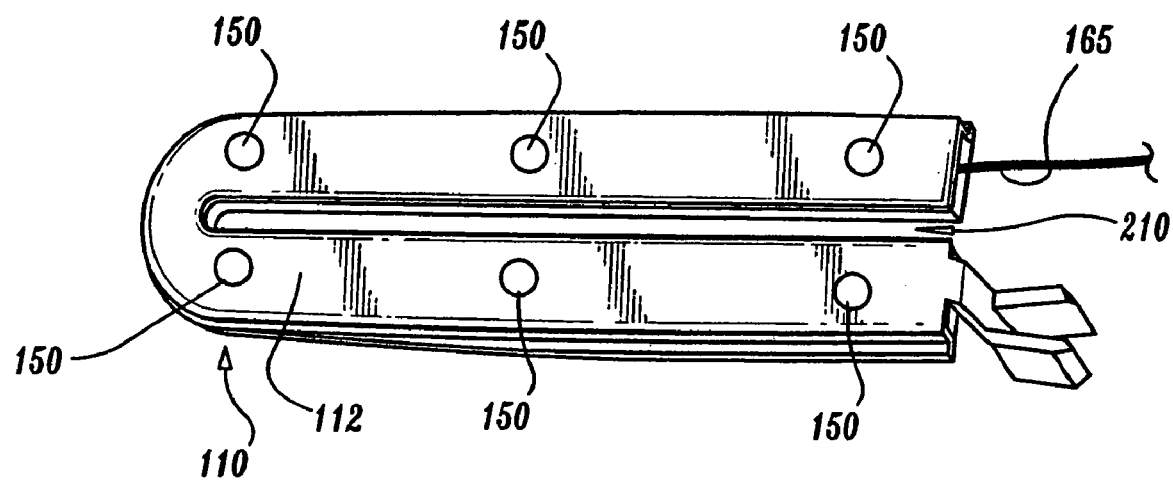
FIG. 4 is an enlarged, perspective view of an electrically conductive sealing plate of the end effector assembly showing a series of selectively adjustable stop members disposed thereon.

As shown in FIGS. 1A-1C, the forceps 10 also includes a trigger 70 which advances a knife 200 disposed within the end effector assembly 100. Once a tissue seal is formed, the user activates the trigger 70 to separate the tissue 400 along the tissue seal. Knife 200 preferably includes a sharpened edge 205 for severing the tissue 400 held between the jaw members 110 and 120 at the tissue sealing site. FIG. 4 shows a longitudinally-oriented channel 210 defined in an electrically conductive sealing plate 112 extending from the proximal end to the distal end thereof. The channel 210 facilitates longitudinal reciprocation of the knife 200 along a preferred cutting plane to effectively and accurately separate the tissue 400 along a formed tissue seal.

The forceps 10 also includes a rotating assembly 80 mechanically associated with the shaft 12 and the drive assembly (not shown). Movement of the rotating assembly 80 imparts similar rotational movement to the shaft 12 which, in turn, rotates the end effector assembly 100. Various features along with various electrical configurations for the transference of electrosurgical energy through the handle assembly 20 and the rotating assembly 80 are described in more detail in the above-mentioned commonly-owned U.S. patent application Ser. Nos. 10/369,894 and 10/460,926.

As best seen with respect to FIGS. 1A-2, the end effector assembly 100 attaches to the distal end 14 of shaft 12. The jaw members 110 and 120 are preferably pivotable about a pivot 160 from the open to closed positions upon relative reciprocation, i.e., longitudinal movement, of the drive assembly (not shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926.

It is envisioned that the forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 20 and handle assembly 30. In either of these two instances, the forceps 10 may be either partially disposable or reposable, such as where a new or different end effector assembly 100 or end effector assembly 100 and shaft 12 are used to selectively replace the old end effector assembly 100 as needed.

Since the forceps 10 applies energy through electrodes, each of the jaw members 110 and 120 includes an electrically conductive sealing plate 112 and 122, respectively, disposed on an inner-facing surface thereof. Thus, once the jaw members 110 and 120 are fully compressed about the tissue 400, the forceps 10 is now ready for selective application of electrosurgical energy as shown in FIG. 3. At that point, the electrically conductive plates 112 and 122 cooperate to seal tissue 400 held therebetween upon the application of electrosurgical energy. Jaw members 110 and 120 also include insulators 116 and 126 which together with the outer, non-conductive plates of the jaw members 110 and 120 are configured to limit and/or reduce many of the known undesirable effects related to tissue sealing, e.g., flashover, thermal spread and stray current dissipation as shown in FIG. 1C.

Of particular importance to this disclosure is the slow close system which allows the gap "G" disposed between the sealing plates when the jaw members are disposed in a closed position to close at a predetermined rate. This has been determined to enhance tissue sealing especially when sealing larger tissue structures (e.g., lung, liver, bronchus, bowels, etc.). A slow close activation surgical technique involves activating the surgical instrument and thereafter slowly closing the sealing plates 112 and 122 of the jaw members to grasp and apply pressure to the tissue to affect sealing. As can be appreciated, this type of procedure is very difficult to master manually due to the many variables involved with the sealing process and, as a result, the instrument may short or the sealing cycle may complete prior to obtaining the fully closed ratcheted position. Hence, it is preferred that the procedure is automated using a series of sensors and controllers. It is envisioned that an automatic stop member adjustment system (described below) is one way to achieve slow close activation and provide more effective sealing of large tissue structures. The closure rate may be adjusted during activation based upon a continually-sensed surgical condition (e.g., tissue impedance, tissue type, tissue clarity, tissue compliance, etc.) utilizing a feed back control loop or control source 300, and a sensor assembly 170a and 170b and a mechanically retractable/extendable stop member assembly 140.

With respect to this particular embodiment, it is known that sealing of the tissue 400 is accomplished by virtue of a unique combination of gap control, pressure and electrical control. In other words, controlling the intensity, frequency and duration of the electrosurgical energy applied to the tissue through the sealing plate 112 and 122 are important electrical considerations for sealing tissue. In addition, two mechanical factors play an important role in determining the resulting thickness of the sealed tissue and the effectiveness of the seal, i.e., the pressure applied between the opposing jaw members 110 and 120 (between about 3 kg/cm$^2$ to about 16 kg/cm$^2$) and the gap distance "G" between the opposing sealing plates 112 and 122 of the jaw members 110 and 120, respectively, during the sealing process (between about 0.001 inches or higher denoting upon the size of the tissue). A third mechanical factor has recently been discovered which contributes to the quality and consistency of a tissue seal, namely the closure rate of the electrically conductive surfaces or sealing plates during activation.

More particularly, controlling the gap distance "G" between opposing sealing surfaces 112 and 122 directly relates to the closure rate i.e., the closure rate is defined as the rate of change of the gap distance "G." Therefore, adjusting the gap distance "G" allows the user to adjust the closure rate. As discussed in more detail below, the forceps 10 according to the present disclosure controls the gap distance "G" using one technique which allows a user to selectively adjust (i.e., manually, automatically based on sensed surgical conditions or predetermined parameters) the retraction or extension of at least one stop member 150 relative to the surface of the sealing plate, e.g., 112. As a result thereof, adjusting stop member 150 controls the closure rate which, in turn, allows a surgeon to implement a slow close surgical procedure using forceps 10.

More specifically, the rate of closure of the sealing plates 112 and 122 to grasp and/or apply pressure to tissue is regulated by adjusting the gap distance "G" during the surgical procedure. In one particular instance, the stop members 150 are connected to a controller 155 which together comprise a selectively adjustable stop member control unit 145. Each of the stop member control units 145 is connected to the stop member assembly 140 which regulates the gap distance "G" by extending or retracting a plurality of stop members 150 based on the control signals received from the control source 300 and the feedback signals transmitted by a sensor assembly 170a and 170b. The controller 155 electrically, mechanically or electro-mechanically adjusts the distance the stop members 150 project by retracting or extending the stop members 150 from the sealing plate 112. As a result, the gap distance "G" is adjusted by changing the distance that the stop members 150 project from the sealing plate 112. The controller 155 is adapted to receive signals from a control source 300 shown in FIG. 2 which may be attached to an electrosurgical generator 500 or incorporated into the housing of the forceps 10.

As discussed above, the stop member 150 limits the movement of the two opposing jaw members 110 and 120 (and sealing plates 112 and 122) relative to one another by acting as a barrier between the two surfaces. It is envisioned that the stop members 150 may be disposed on one or both of the sealing plates 112 and 122 depending upon a particular purpose or to achieve a particular result. Preferably, the stop members 150 extend from at least one of the sealing plates 112, 122 a predetermined distance according to the specific material properties of the stop member 150 (e.g., compressive strength, thermal expansion, etc.) to yield a consistent and accurate gap distance "G" during sealing.

In order for the stop members 150 to prevent the sealing plates 112, 122 from coming in contact with each other, preferably, the stop members 150 are made from an insulative material, e.g., parylene, nylon and/or ceramic and are dimensioned to limit opposing movement of the sealing plates 112 and 122 to within the above mentioned gap range "G". However, the compressive strength of the material used in manufacturing the stop member 150 should be considered during activation since one material may have to be adjusted differently from another material to achieve the same gap distance "G". For example, the compressive strength of nylon is different from ceramic and, therefore, the nylon material may have to extend a greater distance from the sealing plate 112 to counteract the closing force of the opposing jaw members 110 and 120 and to achieve the same desired gap distance "G". As can be appreciated, these considerations may be automatically regulated or controlled at the control source 300 via a computer algorithm or look up table as discussed in more detail below.

Moreover, it is contemplated that any combination of different stop members 150 may be assembled along the sealing plates 112 (and/or 122) to achieve a desired gap distance "G". A ceramic or insulative coating may be deposited or sprayed onto the tissue engaging plate of the stop member(s) 150. Thermal spraying techniques are contemplated which involve depositing a broad range of heat-resistant and insulative materials on the tissue engaging plates of the stop members 150, high velocity Oxy-fuel deposition, plasma deposition, etc. Examples of stop members 150, control units 145, and stop member assemblies 140 are shown and described in a commonly-owned U.S. patent application Ser. No. 10/846,262 entitled "TISSUE SEALER WITH NON-CONDUCTIVE VARIABLE STOP MEMBERS AND METHOD OF SEALING TISSUE" which is hereby incorporated by reference herein in its entirety.

FIG. 4 shows one exemplary configuration of the stop members 150 disposed on or protruding from the sealing plate 112. It is envisioned that the stop members 150 can be positioned on either or both jaw members 110 and 120 depending upon a particular purpose or to achieve a desired result. More particularly and as illustrated in FIG. 4, a series of longitudinally-oriented tab-like stop members 150 are disposed along either side of the knife channel 210 of jaw member 110. Preferably, the stop members 150 may be configured in any known geometric or polynomial configuration, e.g., triangular, rectilinear, circular, ovoid, scalloped, etc., depending upon a particular purpose.

As shown in FIGS. 1B and 1C, the selectively adjustable stop member assembly 140 is located within at least one of the jaw members 110 or 120. More particularly, at least one of the jaw members, e.g., jaw member 110, includes a cavity 130 disposed therein which is dimensioned to house the stop member assembly 140. The stop member assembly 140 adjusts the distance that each stop member 150 extends from the sealing plate 112 using the controller 155, which cooperate with the stop member 150 in a plurality of ways. For example, each stop member 150 and its corresponding controller 155 may be threadably connected such that the controller 155 "unscrews" the stop member 150 to adjust the distance that the stop member 150 extends from the sealing plate 112. Other mechanical systems are also envisioned to allow selective regulation of the gap distance "G" (e.g., gearing mechanisms, camming mechanisms, pneumatic mechanisms, hydraulic mechanisms, etc.). Electromechanical systems are also contemplated (e.g., electro-mechanical actuators, ferroelectric actuators, piezo-electric actuators, piezo-ceramic actuators, magnetostrictors, thermomechanical systems [e.g., smart materials, shape memory alloys, etc.], and rotational actuators, etc.).

One version presently envisioned is a slow close activation system which is intended to include the sealing plates 112, 122, stop member(s) 150 and electrical generator 500 will now be discussed. This system involves the stop member assembly 140 being controlled automatically by the control source 300 based on the feedback received from the sensors 170a and 170b. The sensors 170a and 170b form a part of a closed-loop control system which automatically adjusts the forceps 10 prior to and/or during activation based on pre-surgical parameters and continually-sensed parameters. The sensors 170a and 170b are connected to the control source 300 (or electrosurgical generator) via cables 171a and 171b, respectively. One example of a closed-loop control system is described in commonly-owned U.S. patent application Ser. No. 10/427,832 filed on May 1, 2003 entitled "METHOD AND SYSTEM FOR CONTROLLING OUTPUT OF RF MEDICAL GENERATOR" the entire contents of which are hereby incorporated by reference herein.

In the slow-close activation system, the stop member(s) 150 are adjusted during activation based upon a continually-sensed surgical condition (e.g., tissue impedance, tissue type, tissue clarity, tissue compliance, etc.) utilizing a feed back control loop. It is envisioned that this may allow the control system to regulate the rate of closure of the sealing plates 112 and 122 upon tissue. Initially, the surgeon grasps the tissue in a customary manner and fully ratchets the forceps about the tissue within the preferred pressure ranges so that the stop member(s) 150 are extended out of the jaw members 110 (and/or 120) to achieve the desired gap distance "G".

The preferred gap distance "G" may be selected from a look-up table during manual adjustment or determined by a computer algorithm stored within the control source 300 during automatic adjustment. For example, a relatively small gap distance "G" would be used in sealing a plurality of small blood vessels, while a larger gap distance "G" is preferable when sealing thicker tissue, such as an organ. The gap distance "G" between opposing sealing plates 112 and 122 during sealing preferably ranges from about 0.001 inches to about 0.008 inches. For smaller tissue types the gap distance is preferably between about 0.002 inches to about 0.003 inches and for larger tissue types the gap distance is preferably between about 0.004 inches to about 0.007 inches.

Once the tissue 400 is grasped between the jaw members 110 and 120 the slow closure process commences which involves retraction of the stop members 150. As the stop members 150 are retracted into the jaw members 110 and/or 120 the gap distance "G" decreases and a seal results. Therefore, the rate of closure of the sealing plates 112 and 122 is directly related to the changes in the gap distance "G" which, in turn, depends on the rate of retraction of the stop member(s) 150 into the jaw member(s) 110 and/or 120. Hence, regulation of the retraction rate of the stop member(s) 150 directly regulates the rate of closure of the sealing plates 112 and 122.

The stop members 150 are retracted at a predetermined rate which may be adjusted manually by the surgeon (e.g., adjusting a control knob 350 shown in FIG. 2) or preferably automatically, by the control source 300 based on the feedback signals (e.g., based upon tissue thickness, tissue temperature, tissue impedance, tissue moisture, tissue clarity, tissue compliance during activation, etc.) sent by the sensors 170a and 170b. For instance, the stop members 150 can be programmed to activate in a slow close manner by automatically adjusting from a large gap distance e.g., about 0.10 inches or larger to within a preferred gap range of about 0.001 inches to about 0.008 inches during activation. As can be appreciated, this enables any surgeon to perform a slow close technique for sealing large tissue structures.

It is also envisioned that the slow close technique may be accomplished utilizing a fixed stop member configuration and spring-like sealing plates. As can be appreciated, in this instance, the stop members are configured to project or extend a fixed distance from the sealing plate or plates 112 to prevent the sealing pates fro touching one another and shorting. The sealing plate, e.g., 112 (or sealing plates 112 and 122) is configured to include one or more springs 149a, 149b (or a spring assembly) which mount between the sealing plates 112 and 126 and the jaw housing 116 and 126, respectively. It is contemplated that the springs 149 allow the sealing plates 112 and 122 to slowly flex to accommodate the pressure applied to the tissue until a specified closure pressure is obtained (preferably within the above-identified working range of about 3 kg/cm2 to about 16 kg/cm2). As can be appreciated, the spring rates can be predetermined for optimal tissue effect based upon tissue type or tissue thickness. In addition, mechanical features may be included which allow the spring tension rates to be adjusted according to sensory feedback information from the generator via sensors 170a and 170b or manual input from the surgeon.

It is envisioned that any type of spring 149a, 149b may be utilized to accomplish this purpose or, alternatively, a layer of visco-elastic or elastomeric or smart material may be disposed between the sealing plates and the jaw housing to provide a specified spring rate. In this instance, gamma radiation sterilization techniques would obviously compromise the visco-elastic or elastomeric material and, as such, other sterilization techniques are envisioned that would maintain the integrity of the visco-elastic or elastomeric material, e.g., ethylene oxide sterilization.

Figure 5:
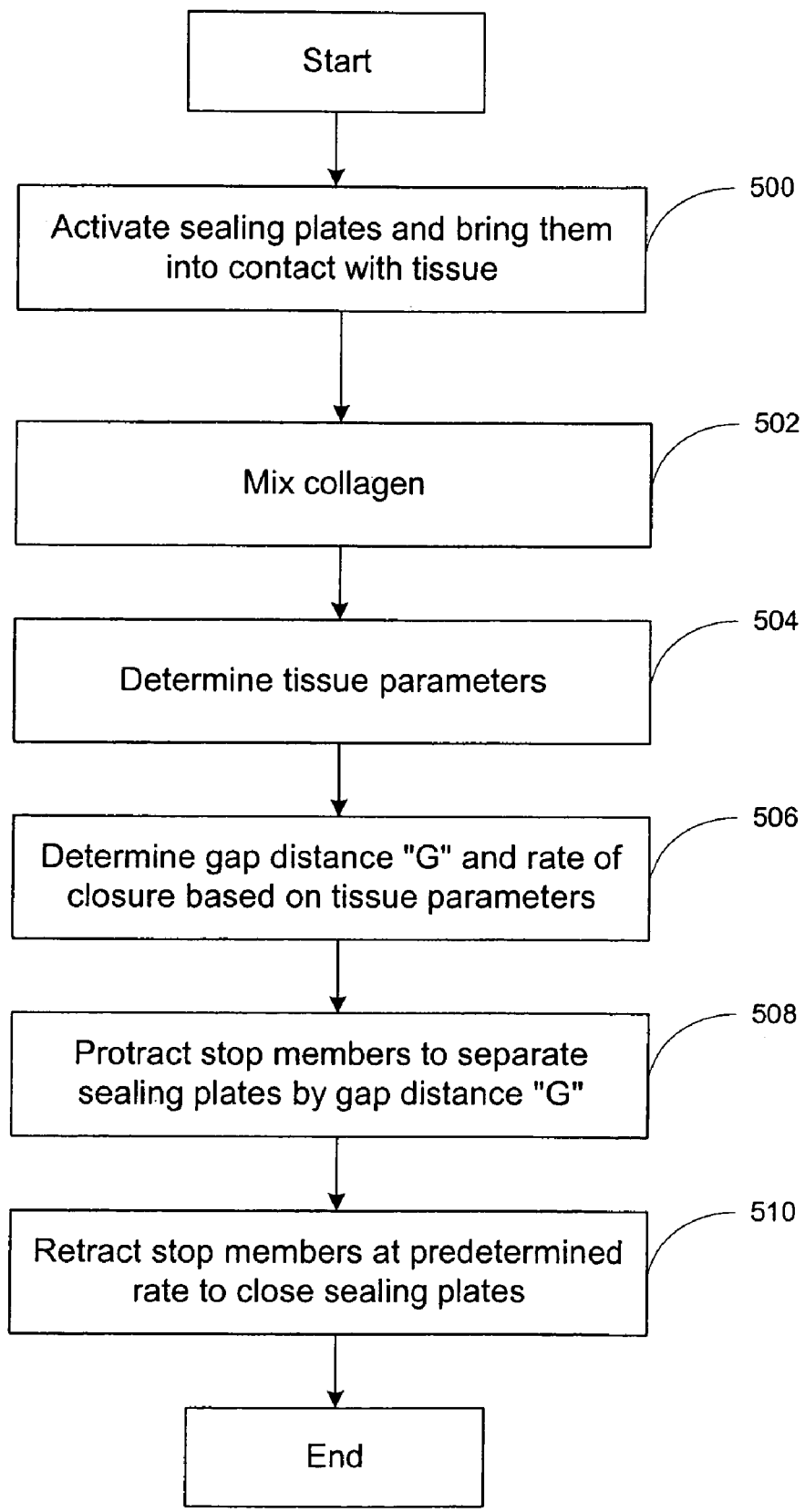
FIG. 5 shows a flow chart showing a sealing method using the endoscopic bipolar forceps of FIGS. 1A-4.
Figure 6:
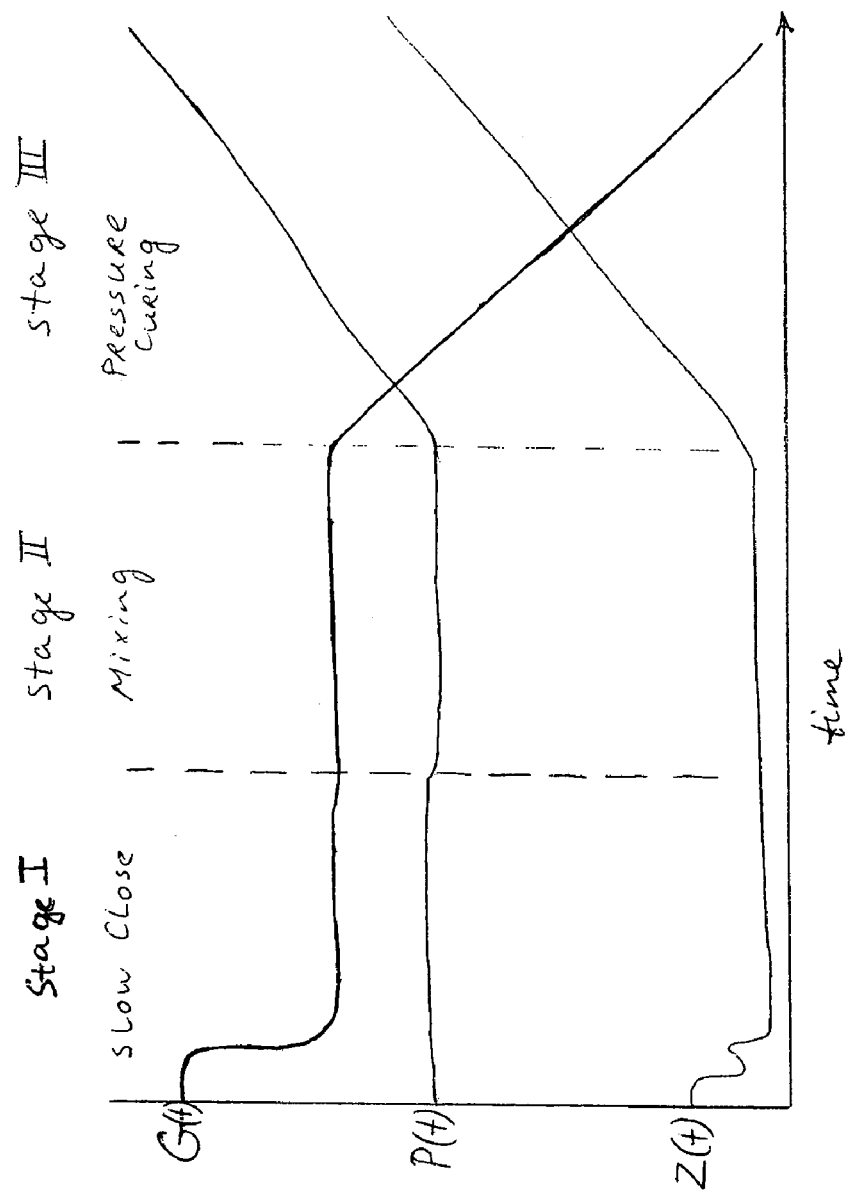
FIG. 6 shows a graph illustrating the changes occurring to collagen during sealing utilizing the method shown in FIG. 5.
Figure 7:
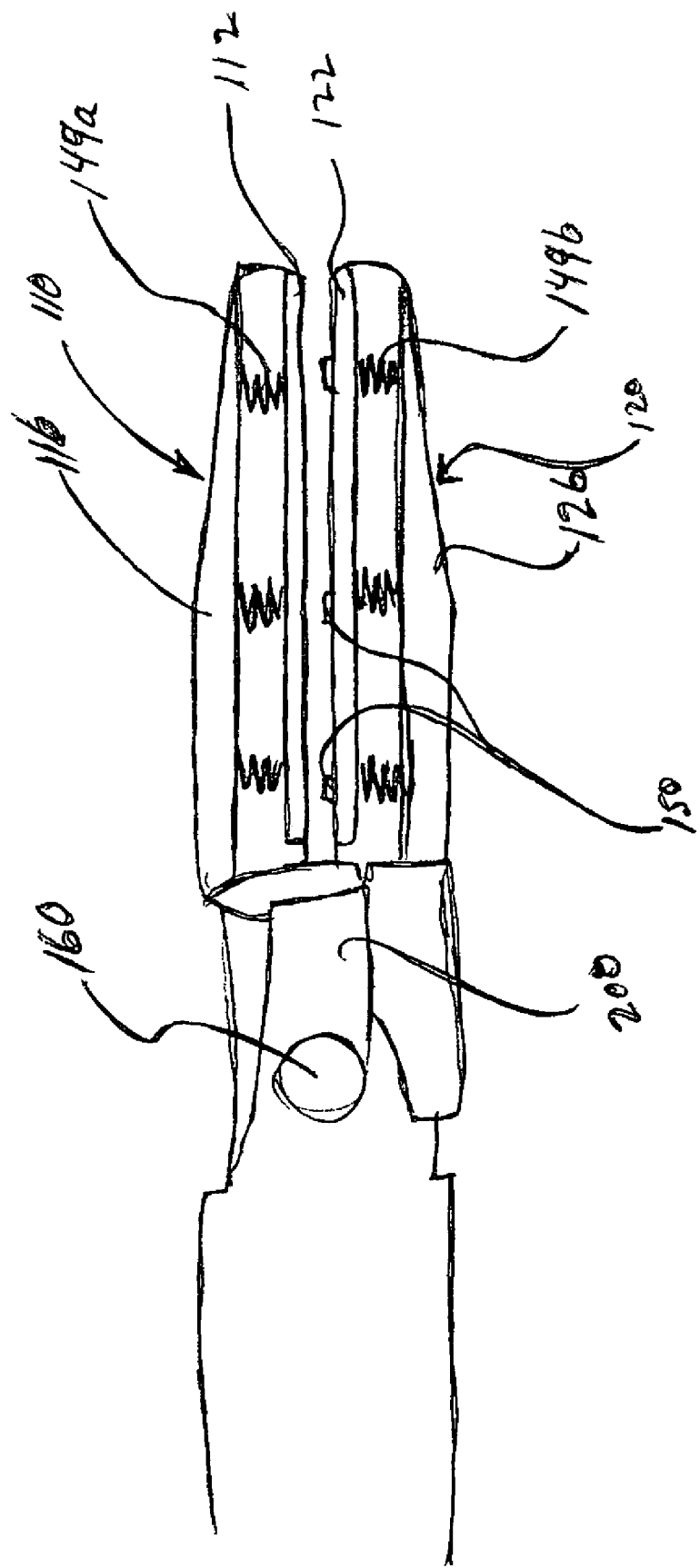
FIG. 7 is a side, partial internal view of an end effector assembly including a slow close spring mechanism shown in closed configuration.

The sealing method according to the present disclosure is shown in FIG. 5. In addition, FIG. 6 shows a graph illustrating the changes that are contemplated to occur to collagen when it is subjected to sealing using the method of FIG. 5. Line G(t) represents the gap distance "G" as it changes over time, line P(t) represents the pressure applied to the tissue being sealed over time, and line Z(t) represents the electrosurgical energy applied during a specified time period.

In step 500, the forceps 10 grasps and begins to apply pressure to the tissue 400 using the jaw members 110 and 120. This is shown as Stage I in FIG. 6, during which time the sealing plates 112 and 122 are activated and are in contact with the tissue 400 but are not fully closed. This is represented by the sharp decline in the line G(t) during Stage I, which then rapidly levels off. When the sealing plates 112 and 122 contact the tissue 400 electrosurgical energy is applied thereto and the collagen contained therein is denatured and becomes more mobile (i.e., liquefies). Although electrosurgical energy is being applied, little pressure is applied to create a seal, this is shown by a straight horizontal line P(t). Simultaneously, the water contained within the tissue 400 is allowed to escape from the sealing site. As a result, the peak temperature at which a seal is created is reduced.

In step 502, the previously melted collagen is mixed in order to allow for its structural components (e.g., polymers) to intertwine as shown in Stage II. Mixing can be achieved by applying electrosurgical energy of predetermined frequency and to the sealing site through the sealing plates 112 and 122 under a predetermined pressure. The optimum frequency and amplitude of the waves depends on the collagen structures which are being mixed and may be automatically controlled as specified above. This is shown as Stage II, where the line G(t), line P(t), and line Z(t) are all generally unchanged, representing that the gap distance, the pressure, and the electrosurgical energy remain generally constant.

Once the collagen is mixed, it is further cured by applying electrosurgical energy and pressure as shown in Stage II. During Stage III the gap distance "G" decreases at a predetermined rate (e.g., the rate of closure is the slope of the line G(t)), while the pressure (e.g., line P(t)) and the electrosurgical energy (e.g., line Z(t)) are increased. The pressure is preferably increased at a rate that is slow enough to result in an effective seal but not fast enough to force the forming collagen mass outside of the sealing site. As discussed above, one of the presently envisioned ways the rate at which the gap distance "G" and the sealing plates 112 and 122 are closed is controlled by the control source 300 through the stop member assembly 140, which retracts the plurality of the stop members 150 through the controllers 155. This rate at which the stop member assembly 140 decreases the distance gap "G" may be determined automatically based on the readings of the sensor assembly 170a and 170b.

In step 504, the sensors 170a and 170b sense a parameter such as tissue type, tissue thickness, tissue compliance, and/or tissue impedance and transmit that information to the control source 300. Based on the algorithms and data contained therein, in step 506, the control source 300 selects the ideal gap distance "G" for the tissue to be sealed as well as the rate at which the sealing plates 112 and 122 will close. This may also directly relate to the ideal rate of closure pressure. These calculations are transmitted to the stop member assembly 140 which, in step 508, extends or protracts the stop members 150 so that the sealing plates 112 and 122 are separated by the gap distance "G" once the jaw members 110 and 120 are closed. Once this is accomplished, in step 510, the sealing plates 112 and 122 close at the rate determined by the source controller 300, i.e., the stop member assembly 140 signals the controllers 155 to retract the stop members 150 at the predetermined rate ensuring that the rate is slow enough to retain the collagen mass at the site resulting in an effective seal.

It is envisioned that step 508 may be eliminated in the instance where the stop members 150 or stop member assembly 140 is configured to return to a preset extended condition relative to the sealing plates 112 and 122 each time the jaw members 110 and 120 are opened to grasp/manipulate tissue. It is also envisioned that the stop members may manually or automatically be extended or locked for non-slow close sealing such as those procedures described in any of the aforementioned commonly owned applications.

The apparatus and method according to the present disclosure allow for tissue sealing procedures which retain the collagen at the sealing site which is known to enhance the consistency, effectiveness, and strength of tissue seals. This is accomplished by using a slow close activation to initially denature the collagen and then close the sealing plates under pressure at a predetermined rate with limited extrusion of the cured and mixed collagen mass from the sealing site which contributes to an effective and uniform seal.

Figure 8:
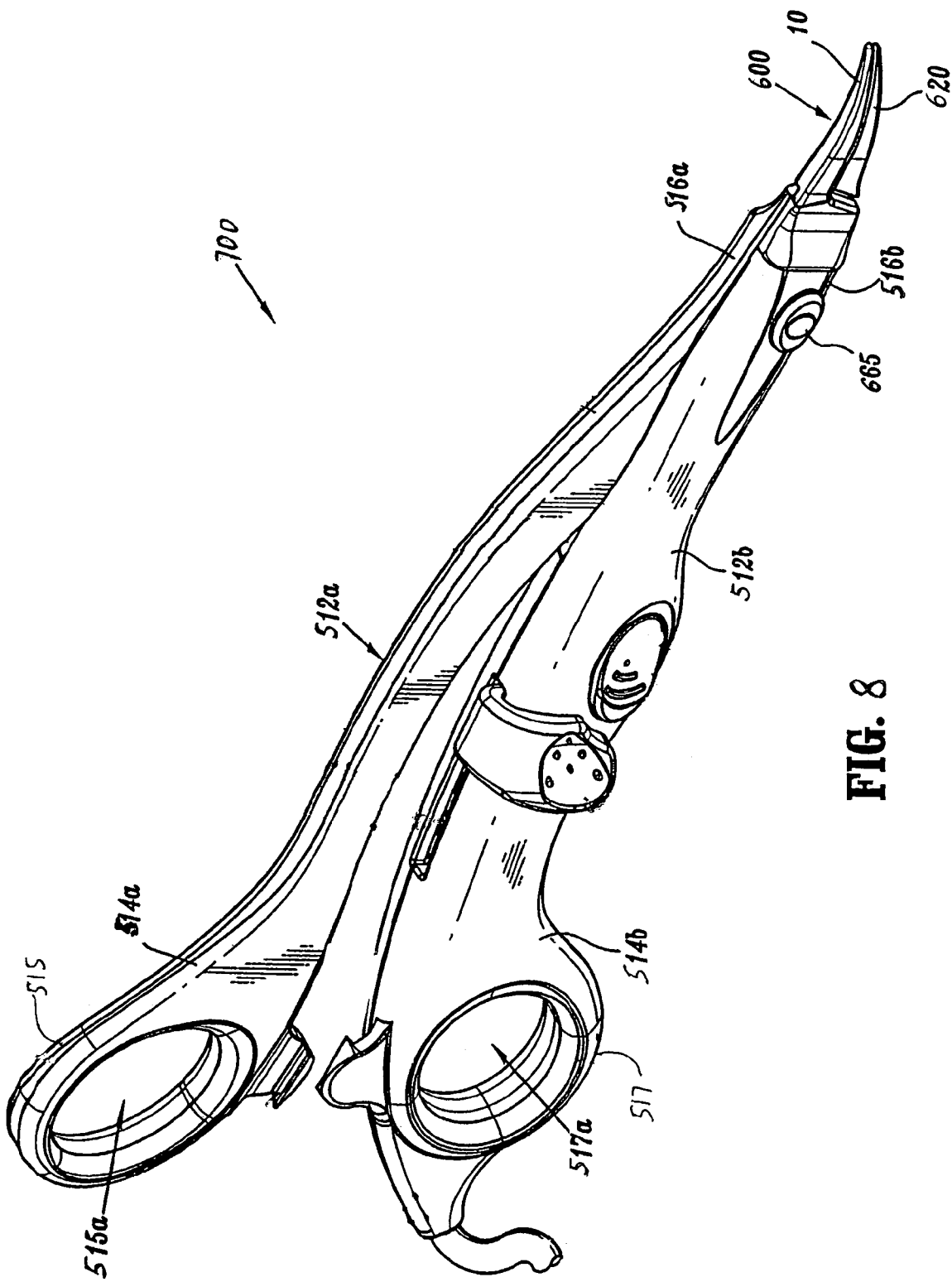
FIG. 8 is a perspective view of an open bipolar forceps which is configured to close at a predetermined rate according to the present disclosure.

From the foregoing and with reference to the various figure drawings, those skilled in the art will appreciate that certain modifications can also be made to the present disclosure without departing from the scope of the same. For example and as mentioned above, it is contemplated that any of the slow closure techniques, methods and mechanisms disclosed herein may be employed on an open forceps such as the open forceps 700 disclosed in FIG. 8. The forceps 700 includes an end effector assembly 600 which attaches to the distal ends 516a and 516b of shafts 512a and 512b, respectively. The end effector assembly 600 includes pair of opposing jaw members 610 and 620 which are pivotally connected about a pivot pin 665 and which are movable relative to one another to grasp vessels and/or tissue. A stop member assembly such as the stop member assembly 140 described with respect to FIGS. 1-7 and/or a series of sensors 170a and 170b may be disposed within the end effector 600 to create a slow close option for the surgeon. In addition, the generator (not shown) which supplies power to the forceps 700 may be configured to automatically regulate the stop member assembly 140 (or other types of slow close mechanisms described above) or the surgeon may opt to manually control the closing of the seal plates onto the tissue as described above.

Each shaft 512a and 512b includes a handle 515 and 517, respectively, disposed at the proximal end 514a and 514b thereof which each define a finger hole 515a and 517a, respectively, therethrough for receiving a finger of the user. Finger holes 515a and 517a facilitate movement of the shafts 512a and 512b relative to one another which, in turn, pivot the jaw members 610 and 620 from an open position wherein the jaw members 610 and 620 are disposed in spaced relation relative to one another to a clamping or closed position wherein the jaw members 610 and 620 cooperate to grasp tissue or vessels therebetween. Further details relating to one particular open forceps are disclosed in commonly-owned U.S. application Ser. No. 10/962,116 filed Oct. 8, 2004 entitled "OPEN VESSEL SEALING INSTRUMENT WITH CUTTING MECHANISM AND DISTAL LOCKOUT", the entire content of which being incorporated by reference herein.

In addition, it is also contemplated that the presently disclosed forceps may include an electrical cutting configuration to separate the tissue either prior to, during or after cutting. One such electrical configuration is disclosed in commonly-assigned U.S. patent application Ser. No. 10/932,612 entitled "Vessel Sealing Instrument With Electrical Cutting Mechanism" the entire contents of which being incorporated by reference herein.

Furthermore, it is envisioned that the forceps 10 or 700 may be configured to include a manual slow close mechanism, rotating wheel or slide which upon manual activation thereof retract the stop members relative to the sealing plates after the handle has been ratcheted and during activation. Moreover, another method may allow the surgeon to grasp and close the forceps about the tissue (within the specified pressure range) and upon activation of the switch (foot switch or hand switch) the stop members automatically retract based upon sensed surgical conditions or a preset algorithm or by preset electro-mechanical action.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. Electrosurgical bipolar forceps for sealing tissue, comprising:
    at least one shaft member having an end effector assembly disposed at a distal end thereof, the end effector assembly including jaw members movable from a first position in spaced relation relative to one another to at least one subsequent position wherein the jaw members cooperate to grasp tissue therebetween; and
    each of the jaw members including a sealing plate which communicates electrosurgical energy through tissue held therebetween, at least one of the sealing plates including at least one adjustable stop member coupled to at least one controller, the at least one adjustable stop member configured to separate the sealing plates by a predetermined gap distance and the at least one controller configured to adjust the at least one adjustable stop member to close the sealing plates at a predetermined rate.

2. The electrosurgical bipolar forceps for sealing tissue as in claim 1, wherein the at least one controller is threadably coupled to the at least one adjustable stop member.

3. The electrosurgical bipolar forceps for sealing tissue as in claim 1, further comprising:
    a knife channel defined along a length of at least one of the jaw members, the knife channel being dimensioned to reciprocate a cutting mechanism therealong; and
    an actuator operatively connected to one of the shaft members for selectively advancing the cutting mechanism from a first position wherein the cutting mechanism is disposed proximal to tissue held between the jaw members to at least one subsequent position wherein the cutting mechanism is disposed distal to tissue held between the jaw members.

4. The electrosurgical bipolar forceps as in claim 1, wherein the at least one controller which adjusts the at least one adjustable stop member includes at least one mechanism selected from a group consisting of gearing mechanisms, camming mechanisms, pneumatic mechanisms, hydraulic mechanisms, electro-mechanical actuators, ferroelectric actuators, piezo-electric actuators, piezo-ceramic actuators, magnetostrictors, and rotational actuators.

5. The electrosurgical bipolar forceps for sealing tissue according to claim 1 further comprising:
    a sensor assembly which determines at least one pre-surgical tissue parameter and transmitting data pertaining to at least one tissue parameter to an electrosurgical energy source; and
    a control source which determines the gap distance and the predetermined rate as a function of at least one tissue parameter and which transmits control signals to the at least one controller.

6. The electrosurgical bipolar forceps for sealing tissue according to claim 5, wherein the at least one tissue parameter is chosen from a group consisting of tissue type, tissue thickness, tissue compliance, and tissue impedance.

7. A method for sealing tissue comprising the steps of:
    providing electrosurgical bipolar forceps having an end effector assembly attached at a distal end thereof, the end effector assembly including jaw members, each of the jaw members including a sealing plate, at least one of the sealing plates including at least one adjustable stop member coupled to at least one controller;
    determining at least one pre-surgical parameter;
    extending the at least one adjustable stop member to adjust a gap distance between the jaw members based upon the at least one pre-surgical parameter;
    actuating the jaw members to grasp tissue between the sealing plates;
    conducting energy to the sealing plates though the tissue grasped therebetween; and
    retracting the at least one adjustable stop member at a predetermined rate based upon the at least one pre-surgical parameter to effect a tissue seal.

8. The method according to claim 7, further comprising the steps of:
    determining the at least one pre-surgical parameter with a sensor assembly;
    transmitting data pertaining to the at least one pre-surgical parameter to a control source;

determining the gap distance and the predetermined rate as a function of the at least one pre-surgical parameter; and transmitting control signals from the control source to the at least one controller.

9. The method according to claim 7, wherein the at least one pre-surgical parameter is chosen from a group consisting as tissue type, tissue thickness, tissue compliance, and tissue impedance.

10. The method according to claim 7, wherein the at least one controller includes at least one mechanism selected from a group consisting of gearing mechanisms, camming mechanisms, pneumatic mechanisms, hydraulic mechanisms, electro-mechanical actuators, ferroelectric actuators, piezo-electric actuators, piezo-ceramic actuators, magnetostrictors, and rotational actuators.

* * * * *